United States Patent [19]

Aoyama et al.

[11] Patent Number: 4,978,615
[45] Date of Patent: Dec. 18, 1990

[54] METHOD FOR THE DETERMINATION OF THE COMPOUND HAVING MERCAPTO GROUP

[75] Inventors: Norihito Aoyama; Akira Miike; Yoshiaki Shimizu, all of Shizuoka; Toshio Tatano, Numazu, all of Japan

[73] Assignee: Kyowa Medex Co., Ltd., Tokyo, Japan

[21] Appl. No.: 157,141

[22] Filed: Feb. 10, 1988

Related U.S. Application Data

[63] Continuation of Ser. No. 721,951, Apr. 11, 1985, abandoned.

[30] Foreign Application Priority Data

Apr. 13, 1984 [JP] Japan .................. 59-74714

[51] Int. Cl.⁵ .................. C12Q 1/28; C12Q 1/26; C12Q 1/00
[52] U.S. Cl. .................. 435/25; 435/25; 435/26; 435/28; 435/810
[58] Field of Search .................. 435/25, 4, 26, 28, 810

[56] References Cited

U.S. PATENT DOCUMENTS

| | | | |
|---|---|---|---|
| 2,905,594 | 9/1959 | Morris | 435/28 |
| 4,036,863 | 7/1977 | Karger | 260/386 |
| 4,448,446 | 5/1984 | Flores | 346/224 |
| 4,592,996 | 6/1986 | Yamanishi | 435/11 |
| 4,613,465 | 9/1986 | Yamanishi | 260/394 |
| 4,673,635 | 6/1987 | Yamanishi et al. | 435/28 X |

FOREIGN PATENT DOCUMENTS

| | | | |
|---|---|---|---|
| 0057661 | 8/1982 | European Pat. Off. | |
| 0100217 | 2/1984 | European Pat. Off. | |
| 153872 | 9/1985 | European Pat. Off. | 435/28 |
| 162685 | 11/1985 | European Pat. Off. | 435/28 |
| 2944498 | 5/1980 | Fed. Rep. of Germany | |
| 0008797 | 1/1982 | Japan | |

OTHER PUBLICATIONS

*Chemical Abstracts*, vol. 90, No. 23 (1979), 182296q.

*Primary Examiner*—Esther L. Kepplinger
*Assistant Examiner*—Laurie A. Scheiner
*Attorney, Agent, or Firm*—Fitzpatrick, Cella, Harper & Scinto

[57] ABSTRACT

The present invention provides a method for the determination of a compound having mercapto group which comprises reacting the compound with a chromogen represented by the following general formula (I):

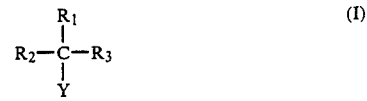

wherein Y is hydrogen or hydroxyl; $R_1$, $R_2$ and $R_3$ may be the same or different, and are groups represented by the following general formula (II), (III) or (IV):

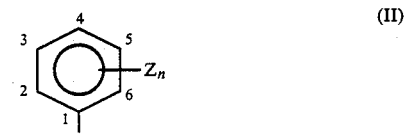

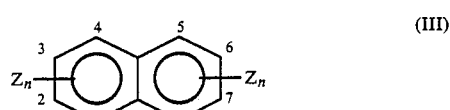

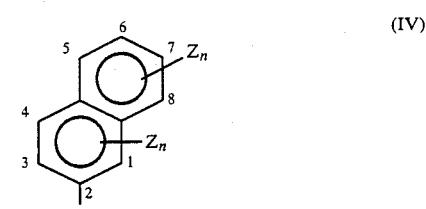

wherein Z (which may be the same or different) is hydroxyl, amino, substituted amino, alkyl, substituted alkyl, alkenyl, aryl, substituted aryl, acyl, halogen, nitro, sulfo, carboxyl or alkoxy; n is 0, 1, 2, or 3; provided that at least one Z in $R_1$, $R_2$ and $R_3$ is hydroxyl, amino, or substituted amino, in the presence of peroxidase or thiol oxide reductase, and determining the pigment thus formed.

13 Claims, No Drawings

METHOD FOR THE DETERMINATION OF THE COMPOUND HAVING MERCAPTO GROUP

This application is a continuation of application Ser. No. 721,951 filed Apr. 11, 1985 now abandoned.

BACKGROUND OF THE INVENTION

The present invention relates to a method and a composition for the determination of a compound having mercapto group (hereinafter referred to as SH compound).

With regard to the determination of SH compound, the following methods have so far been known: (1) titration method using organomercury compound such as p-chloromercury benzoic acid, (2) colorimetric method using sodium nitroprusside and (3) colorimetric method using Ellman's reagents such as 5,5'-dithiobis(2-nitrobenzoic acid) (hereinafter referred to as DTNB).

These methods have the following disadvantages. Method (1) uses organomercury compound, and is much susceptible to influences of living body components in a sample, when applied to clinical inspections, owing to the measurement in the ultraviolet region. In method (2), colored reaction solution is unstable to change of temperature, and wavelength for measurement is low. In method (3), wavelength for measurement is low.

Thus, development of a method for the determination of SH compound with higher accuracy has been desired. As a result of studies to this end, it has been found that a pigment formed by reaction of a compound represented by the general formula (I), as will be described later, with SH compound has a maximum absorption wavelength of about 600 nm and has distinguished characteristics such as less susceptibility to influences of components in a sample, particularly living body components; possible measurement in the visible region; good sensitivity; possible determination of a small amount of a sample; good solubility in water.

SUMMARY OF THE INVENTION

According to the present invention, SH compound can be determined by reacting SH compound with a chromogen represented by the following general formula (I) [hereinafter referred to as compound (I)]:

(I)

wherein Y is hydrogen or hydroxyl; $R_1$, $R_2$ and $R_3$ may be the same or different and are groups represented by the following general formula (II), (III) or (IV):

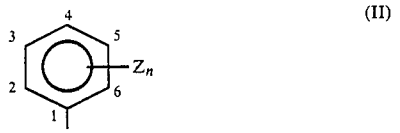

(II)

-continued

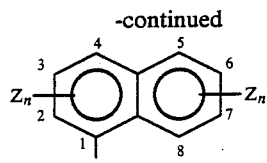

(III)

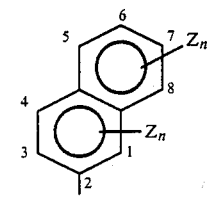

(IV)

wherein Z (all Z's being the same or different) is hydroxyl, amino, substituted amino, alkyl, substituted alkyl, alkenyl, aryl, substituted aryl, acyl, halogen atom, nitro, sulfo, carboxyl or alkoxy; n is 0, 1, 2, or 3; provided that at least one Z in $R_1$, $R_2$, and $R_3$ is hydroxyl, amino or substituted amino, in the presence of peroxidase or thiol oxide reductase, and by determining the pigment thus formed.

DETAILED DESCRIPTION OF THE INVENTION

In the foregoing definitions, the alkyl includes alkyl groups having 1 to 5 carbon atoms such as methyl, ethyl, propyl, butyl, pentyl, etc., the alkenyl includes alkenyl groups having 2 to 5 carbon atoms such as vinyl, propylene, butylene, etc., and the alkoxy includes alkoxy groups having 1 to 4 carbon atoms such as methoxy, ethoxy, propoxy, butoxy, etc.

The aryl is exemplified by phenyl and naphthyl.

The acyl includes acyl groups having 2 to 5 carbon atoms, such as acetyl, propionyl, butyryl, etc., and the halogen includes a chlorine atom, a bromine atom and a fluorine atom.

The substituent in the substituted amino, substituted alkyl, and substituted aryl is exemplified by alkyl, alkenyl, aryl, alkoxy, hydroxyl, carboxyl, sulfo, sulfonyl, halogen atom, amino, alkoxycarbonylamino, alkoxycarbonyl, aminoalkyl, acyl, nitro, etc.

The alkyl, alkenyl, aryl, alkoxy, halogen, acyl, etc. in the substituent have the same meanings as defined above.

The SH compound which can be determined according to the present invention includes L-cysteine, glutathione, coenzyme A (hereinafter referred to as CoA), methanethiol, dihydrolipoamide and thiocholine.

In carrying out the present invention, peroxidase or thiol oxide reductase, and compound (I) are generally added to a buffer solution, for example, Good's buffer, phosphate buffer, borate buffer, acetate buffer and Tris buffer to prepare a reagent solution.

The reagent solution is added to a sample, and subjected to reaction at a temperature of 30° to 50° C. at which the enzyme is not inactivated. Absorption of the reaction solution colored by the pigment thus formed is measured at the maximum absorption wavelength of the pigment in visible ray region on the basis of a reagent blank as a control, and SH compound in the sample is determined from a calibration curve obtained in advance by tests on known amounts of the factor to be determined.

The present method can be applied to the determination of amount of a reactant or enzyme activity in a reaction system producing SH compound by the reaction described later. When the factor to be determined is a compound, the reaction is generally carried out for about 5 to 10 minutes before the absorption measurement, and the desired factor can be determined by colorimetrically measuring the absorption of the reaction solution. When the factor is an enzyme activity, a rate of pigment formation at an appropriate time after the start of reaction is generally determined from changes in the absorbance of reaction solution, whereby the activity can be determined.

The buffer solution is used at a concentration of 10 mM of 1M. Peroxidase and thiol oxide reductase are used at 1 to 500 U/ml. Compound (I) is used at least in an equimolar amount to that of SH compound which reacts with compound (I), and usually at 0.001 to 1 mg/ml.

In the reaction, the concentration of SH compound in a sample is usally adjusted to 0.001 to 1 mg/ml by the reagent solution or distilled water.

When the present invention is applied to a reaction system which produces SH compound, a reactant such as a substrate taking part in the reaction and an enzyme, are used generally at 0.0001 to 100 mg/ml and 10 to 1000 U/ml, respectively, though their amounts often depend on whether they are the objects to be measured or not.

A surfactant such as Triton X-100, etc. can also be used, if required, to clear the solution of turbidity.

Specific examples of compound (I) used in the present invention are shown in Tables 1 to 4 together with their maximum absorption wavelength (λmax) and sensitivity.

Symbols in the Tables show the following groups, and in Tables 1 to 3, the number in parenthesis shows the position.

Determination of sensitivity is carried out in the following manner:

L-cysteine solution: L-cysteine hydrochloride is added to distilled water to make a solution at 20 mg/dl.
Reagent solution: 50 mM phosphate (pH 7.0) buffer containing 10 U/ml peroxidase, 0.1 mg/ml Triton X-100, and 0.2 mg/ml compound (I).

3 ml of reagent solution is added to 20 μl of L-cysteine solution to conduct reaction. OD value is measured at λmax, and the sensitivity is given as a relative value to that obtained by using 5,5'-dithio-bis(2-nitrobenzoic acid) which is used as Ellman's reagent in the determination of mercapto group as 100.

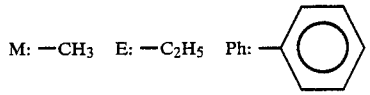

M: —CH₃   E: —C₂H₅   Ph:

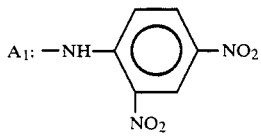

A₁: —NH—⟨⟩—NO₂ (with NO₂)

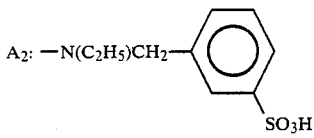

A₂: —N(C₂H₅)CH₂—⟨⟩—SO₃H

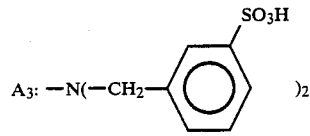

A₃: —N(—CH₂—⟨⟩—SO₃H)₂

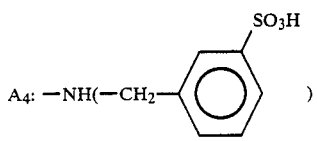

A₄: —NH(—CH₂—⟨⟩—SO₃H)

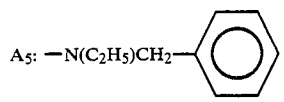

A₅: —N(C₂H₅)CH₂—⟨⟩

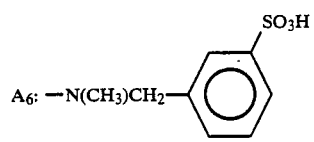

A₆: —N(CH₃)CH₂—⟨⟩—SO₃H

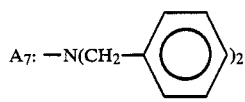

A₇: —N(CH₂—⟨⟩)₂

A₈: —NHC₄H₉

A₉: —NH—⟨⟩—OC₂H₅

A₁₀: —N(C₂H₅)CH₂CH₂SO₃H

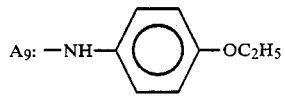

A₁₁: —NH—⟨⟩ (with H₂N)

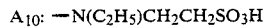

A₁₂: —NH—⟨⟩⟨⟩

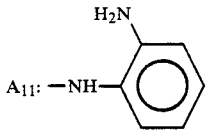

A₁₃: —NH—⟨⟩—NH—⟨⟩

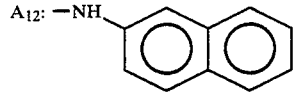

A₁₄: —N(CH₃)—⟨⟩—SO₃H

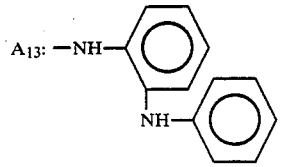

A₁₅: —NH—⟨⟩—CH₃

TABLE 1

| Compound No. | Y | R₁ Formula II | R₂ Formula II | R₃ Formula II |
|---|---|---|---|---|
| 1 | H | OH (2), COOH (5) | NM₂ (4) | NM₂ (4) |
| 2 | OH | " | " | " |
| 3 | H | OH (2), SO₃H (5) | " | " |
| 4 | OH | " | " | " |
| 5 | H | M (2) COOH (5) | " | " |
| 6 | OH | " | " | " |
| 7 | H | A₁ (3) SO₃H (4) (6) | NE₂ (4) | NE₂ (4) |
| 8 | OH | " | " | " |
| 9 | H | Cl (3) | NHM (4) | NHM (4) |
| 10 | OH | " | " | " |
| 11 | H | NO₂ (3), M (6) | A₂ (4) | A₂ (4) |
| 12 | OH | " | " | " |
| 13 | H | A₃ (3) | NM₂ (4) | NM₂ (4) |
| 14 | OH | " | " | " |
| 15 | H | A₄ (3), SO₃H (6) | NE₂ (4) | NE₂ (4) |
| 16 | OH | " | " | " |
| 17 | H | SO₃H (4) (6) OH (3) | A₅ (4) | A₅ (4) |
| 18 | OH | SO₃H (4) (6) OH (3) | " | " |
| 19 | H | SO₃H (3), OH (6) | NM₂ (4) | A₃ (4) |
| 20 | OH | " | " | " |
| 21 | H | Cl (3) (6) | A₆ (4) | A₆ (4) |
| 22 | OH | " | " | " |
| 23 | H | OH (6) | A₇ (4) | A₇ (4) |
| 24 | OH | " | " | " |
| 25 | H | OH (2) | A₈ (4), M (3) | A₈ (4), M (3) |
| 26 | OH | " | " | " |
| 27 | H | A₉ (4) | A₁₀ (4) | A₁₀ (4) |
| 28 | OH | " | " | " |
| 29 | H | A₁₁ (4) | M (2) A₂ (4) | A₂ (4) M (2) |
| 30 | OH | " | " | " |
| 31 | H | M (3), NH₂ (4) | A₁₂ (4) | A₁₂ (4) |
| 32 | OH | " | " | " |
| 33 | H | A₁₃ (4) | A₂ (4) M (2) | A₂ (4) M (2) |
| 34 | OH | " | " | " |
| 35 | H | A₁₄ (4) | A₁₄ (4) | A₁₄ (4) |
| 36 | OH | " | " | " |

TABLE 2

| Compound No. | Y | R₁ Formula II | R₂ Formula II | R₃ Formula II |
|---|---|---|---|---|
| 37 | H | | NM₂ (4) | NHPh (4) |
| 38 | OH | | " | " |
| 39 | H | NM₂ (4) | NM₂ (4) | OH (4), COOH (3), SO₃H (6) |
| 40 | OH | " | " | OH (4), COOH (3), SO₃H (6) |
| 41 | H | " | " | OH (2), SO₃H (3) (6) |
| 42 | OH | " | " | OH (2), SO₃H (3) (6) |
| 43 | H | " | " | OH(2), NHE(4) |
| 44 | OH | " | " | " |
| 45 | H | " | " | A₁₅ (4) |
| 46 | OH | NM₂ (4) | NM₂ (4) | A₁₅ (4) |
| 47 | H | " | " | A₉ (4) |
| 48 | OH | " | " | " |
| 49 | H | " | " | NH₂ (4), SO₃H (3) (6) |
| 50 | OH | " | " | NH₂ (4), SO₃H (3) (6) |
| 51 | H | " | " | OH (2), SO₃H (3) |
| 52 | OH | " | " | OH (2), SO₃H (3) |
| 53 | H | " | " | OH (2), SO₃H (8) |
| 54 | OH | " | " | OH (2), SO₃H (8) |
| 55 | H | " | " | A₁₂ (4) |
| 56 | OH | " | " | " |
| 57 | H | OH (4), M (3), COOH (5) | OH (4), M (3), COOH (5) | OH (2), SO₃H (3) (6) |
| 58 | OH | OH (4), M (3), COOH (5) | OH (4), M (3), COOH (5) | OH (2), SO₃H (3) (6) |
| 59 | H | NM₂ (4) | NM₂ (4) | OH (2) (7) |
| 60 | OH | " | " | " |
| 61 | H | " | " | OH (2) (7), SO₃H (6) |
| 62 | OH | " | " | OH (2) (7), SO₃H (6) |
| 63 | H | " | " | OH (2) |
| 64 | OH | " | " | " |
| 65 | H | " | " | OH (2), SO₃H (7) |
| 66 | OH | " | " | OH (2), SO₃H (7) |

TABLE 3

| Compound No. | Y | R₁ Formula II | R₂ Formula II | R₃ Formula II |
|---|---|---|---|---|
| 67 | H | NHM (4) | NHM (4) | OH (1), SO₃H (3) (5) |
| 68 | OH | " | " | " |
| 69 | H | NM₂ (4) | NM₂ (4) | OH (1), SO₃H (4) |
| 70 | OH | " | " | " |
| 71 | H | " | " | OH (1), SO₃H (3) (6) |
| 72 | OH | " | " | " |
| 73 | H | " | " | OH (1) (5) |
| 74 | OH | " | " | " |
| 75 | H | " | " | OH (1), SO₃H (3) |
| 76 | OH | " | " | " |
| | | R₁:II | R₂:III | R₃:III |
| 77 | H | | OH (4), COOH (3) | OH (4), COOH (3) |
| 78 | OH | | OH (4), COOH (3) | " |

TABLE 4

| Compound No. | λmax (nm) | Sensitivity |
|---|---|---|
| 1 | 615 | 55 |
| 2 | 615 | 55 |
| 3 | 623 | 220 |
| 4 | 623 | 220 |
| 5 | 620 | 75 |
| 6 | 620 | 75 |
| 7 | 630 | 150 |
| 8 | 630 | 150 |
| 9 | 630 | 100 |
| 10 | 630 | 100 |
| 11 | 633 | 240 |
| 12 | 633 | 240 |
| 13 | 627 | 340 |
| 14 | 627 | 340 |
| 15 | 628 | 280 |
| 16 | 628 | 280 |
| 17 | 615 | 80 |
| 18 | 615 | 80 |
| 19 | 635 | 470 |
| 20 | 635 | 470 |
| 21 | 618 | 40 |
| 22 | 618 | 40 |
| 23 | 633 | 850 |
| 24 | 633 | 850 |
| 25 | 645 | 560 |
| 26 | 645 | 560 |
| 27 | 598 | 90 |
| 28 | 598 | 90 |
| 29 | 618 | 160 |
| 30 | 618 | 160 |
| 31 | 631 | 80 |
| 32 | 631 | 80 |
| 33 | 653 | 75 |
| 34 | 653 | 75 |
| 35 | 647 | 100 |

TABLE 4-continued

| Compound No. | λmax (nm) | Sensitivity |
|---|---|---|
| 36 | 647 | 100 |
| 37 | 617 | 90 |
| 38 | 617 | 90 |
| 39 | 598 | 65 |
| 40 | 598 | 65 |
| 41 | 633 | 1500 |
| 42 | 633 | 1500 |
| 43 | 640 | 940 |
| 44 | 640 | 940 |
| 45 | 595 | 375 |
| 46 | 595 | 375 |
| 47 | 644 | 660 |
| 48 | 644 | 660 |
| 49 | 590 | 150 |
| 50 | 590 | 150 |
| 51 | 634 | 260 |
| 52 | 634 | 260 |
| 53 | 630 | 280 |
| 54 | 630 | 280 |
| 55 | 615 | 110 |
| 56 | 615 | 110 |
| 57 | 605 | 200 |
| 58 | 605 | 200 |
| 59 | 635 | 1300 |
| 60 | 635 | 1300 |
| 61 | 633 | 1400 |
| 62 | 633 | 1400 |
| 63 | 634 | 375 |
| 64 | 634 | 375 |
| 65 | 633 | 95 |
| 66 | 633 | 95 |
| 67 | 643 | 525 |
| 68 | 643 | 525 |
| 69 | 633 | 225 |
| 70 | 633 | 225 |
| 71 | 625 | 510 |
| 72 | 625 | 510 |
| 73 | 633 | 525 |
| 74 | 633 | 525 |
| 75 | 635 | 410 |
| 76 | 635 | 410 |
| 77 | 628 | 140 |
| 78 | 628 | 140 |
| DTNB | 530 | 100 |

Compound (I) is a compound known as an intermediate for dye synthesis, and the compounds listed in Tables 1 to 3 can be prepared in the following manner:

PROCESS 1

4,4′-bis(dimethylamino)benzhydrol is reacted with an equimolar amount of substituted benzene or substituted naphthalene given below in 2 to 10-fold amount of 60% sulfuric acid on the basis of the total starting compounds. The reaction is carried out at 50° to 100° C. with stirring for 2 to 3 hours. Then, 5 to 6-fold amount of cold water of about 5° C. is added to the reaction solution, and the mixture is stirred overnight.

The reaction product is recovered therefrom by filtration washed with 8% sulfuric acid, and dried in vacuo, whereby the desired compound the group Y of which is hydrogen is obtained.

The compound is hydrolized with alkali to obtain the desired compound, the group Y of which is hydroxyl.

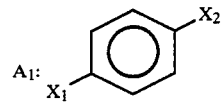

| Compound No. | A | $X_1$ | $X_2$ |
|---|---|---|---|
| 1, 2 | $A_1$ | OH | COOH |
| 3, 4 | " | " | $SO_3H$ |
| 5, 6 | " | $CH_3$ | COOH |

| Compound No. | groups in starting material ($A_2$) |
|---|---|
| 39, 40 | OH(2), COOH(3), $SO_3H(8)$ |
| 41, 42 | $SO_3H(3)$, OH(4) |
| 43, 44 | $NH(C_2H_5)(2)$, OH(4) |
| 49, 50 | $NH_2(2)$, $SO_3H(3)(8)$ |
| 51, 52 | $SO_3H(3)$, OH(4) |
| 53, 54 | OH(4), $SO_3H(6)$ |
| 59, 60 | OH(4)(7) |
| 61, 62 | OH(4)(7) |
| 63, 64 | OH(4)(7) |
| 65, 66 | OH(4), $SO_3H(7)$ |
| 69, 70 | $SO_3H(2)$, OH(5) |
| 71, 72 | $SO_3H(2)$, OH(5) $SO_3H(8)$ |
| 73, 74 | OH(1)(5) |
| 75, 76 | $SO_3H(3)$, OH(5) |

PROCESS 2

Well known pigments corresponding to the individual compounds in the following Table are used as starting compounds and dissolved in 80-fold amount of distilled water on the basis of the weight of the starting compounds. 2-fold amount of sodium boron hydride on the basis of the weight of the starting pigment is slowly added to the individual pigment solutions to conduct reduction reaction. After stirring at room temperature for about 2 hours, the reaction solutions are concentrated to dryness in a rotary evaporator. Then, dried residues are dissolved in a minimum necessary amount of distilled water for dissolving the dried residues. The solution is charged on the column packed with 15 to 20-fold volume of resin HP-20 on the basis of the solution. Then, 3 to 4-fold volume of distilled water on the basis of the resin used is passed therethrough to remove the remaining sodium boron hydride. At that time, the desired products remain as adsorbed on HP-20. Then, a developing solvent of methanol: distilled water = 1:1 is passed therethrough to recover the eluate in appropriate fractions. After the desired compound in the eluate is ascertained by UV monitor or by TLC, the fractions containing the compound are joined together, and concentrated to dryness, to obtain the desired compound, the group Y of which is hydrogen. The compound is hydrolized with alkali to obtain the desired compound, the group Y of which is hydroxyl.

| Compound No. | Color index No | Compound No. | Color index No. | Compound No. | Color index No. |
|---|---|---|---|---|---|
| 7, 8 | 42050 | 77, 78 | 44530 | 35, 36 | 42790 |
| 13, 14 | 42038 | 29, 30 | 42635 | 15, 16 | 42046 |
| 55, 56 | 44095 | 31, 32 | 42700 | 17, 18 | 42052 |
| 57, 58 | 44100 | 33, 34 | 42715 | 37, 38 | 44000 |
| 45, 46 | 44085 | 47, 48 | 44065 | 27, 28 | 42675 |

PROCESS 3

Preparation of compounds Nos. 9, 10, 67 and 68:

At first, 4,4'-bis(dimethylamino)benzhydrol and chlorobenzene (compounds Nos. 9 and 10) or 1-naphthol-3,5-disulfonic acid (compounds Nos. 67 and 68) are subjected to condensation in the same manner as in Process 1 above, using 60% sulfuric acid. The compounds thus obtained are dissolved in an appropriate amount of acetic acid, and one of the two methyl groups is released from the dimethylamino group using lead oxide as a catalyst, whereby compound No. 9 or 67 is obtained. Compound No. 10 or 68 is obtained by hydrolysis of compound No. 9 or 67 with alkali.

PROCESS 4

Preparation of compounds Nos. 11 and 12:

At first, 2-methyl-5-nitrobenzaldehyde and α-(N-methylanilino)-m-toluenesulfonic acid are added in a molar ratio of 1:2 to 10-fold amount of sulfuric acid on the basis of the weight of total starting compounds and the mixture is stirred at about 100° C. for 120 hours. The precipitates are immediately filtered through a glass filter, washed with 5% sulfuric acid, and dried in vacuo, whereby compound No. 11 is obtained. Compound No. 12 is obtained by hydrolysis of compound No. 11 with alkali.

PROCESS 5

Preparation of compounds Nos. 19 and 20:

At first, 2-hydroxybenzaldehyde, N,N-dimethylaniline and N-phenylbenzylamine are added in a molar ratio of 1:1:1 to 10-fold amount of 80% sulfuric acid on the basis of the weight of total starting compounds, and the mixture is stirred at about 190° C. for 120 hours. The precipitates are immediately filtered through a glass filter, washed with 5% sulfuric acid, and dried in vacuo to obtain compound No. 19. Compound No. 20 is obtained by hydrolysis of compound No. 19 with alkali.

PROCESS 6

Preparation of compounds Nos. 21 and 22:

At first, 2,5-dichlorobenzaldehyde and α-(N-methylanilino)-m-toluenesulfonic acid are added in a molar ratio of 1:2 to 10-fold amount of sulfuric acid on the basis of the weight of total starting compounds, and the mixture is stirred at about 100° C. for 120 hours. The precipitates are immediately filtered through a glass filter, washed with 5% sulfuric acid and dried in vacuo to obtain compound No. 21. Compound No. 22 is obtained by hydrolysis of compound No. 21 with alkali.

PROCESS 7

Preparation of compounds Nos. 23, 24, 25 and 26:

At first, 2-hydroxybenzaldehyde and N-phenyldibenzylamine (Nos. 23 and 24), or N-butyl-o-toluidine (Nos. 25 and 26) are added in a molar ratio of 1:2 to 10-fold amount of sulfuric acid on the basis of the weight of starting compounds, and the mixture is stirred at about 100° C. for 120 hours. The precipitates are immediately filtered through a glass filter, washed with 5% sulfuric acid, and dried in vacuo to obtain compound No. 23 or 25. Compound No. 24 or 26 is obtained by hydrolysis of compound No. 23 or 25 with alkali.

Compounds other than those described above can be prepared by selecting the starting compounds according to the desired compounds by said procedures or in the manner as disclosed in the known literature, for example, Color Index, Volume 4.

The present method can be applied to the determination of amount of a reactant or enzyme activity in a reaction system which can stoichiometrically produce SH compound by reaction.

The factors to be determined includes L-aspartate, chloramphenicol, gentamicin $C_{Ia}$, gentamicin $C_I$, choline, cholesterol, L-methionine and NADH. The enzymes the activity of which is to be determined include choline esterase and amino acid acetyltransferase.

These reaction systems are schematically shown as follows and the substrates or the activity of the enzymes in the reaction systems can be determined.

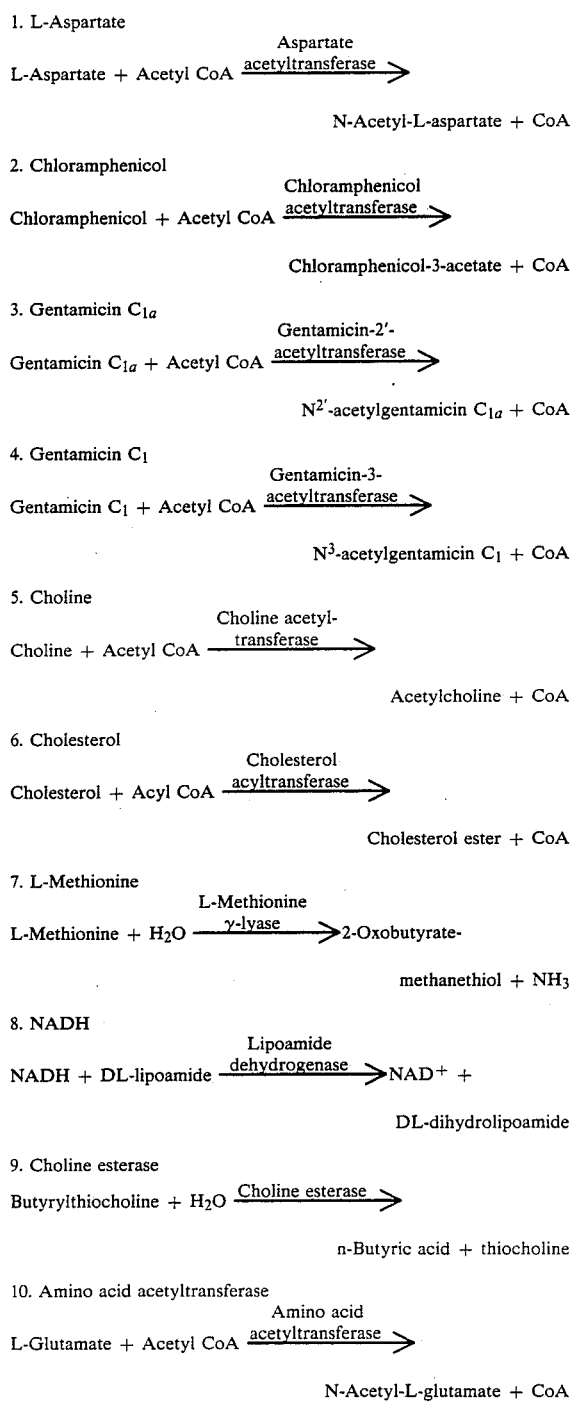

A composition for the determination of SH compound in the present invention comprises (a) peroxidase or thiol oxide reductase, and (b) compound (I). A buffer can be added to the composition, if required.

A composition containing a necessary substrate or enzyme, in view of the factor to be determined or kits separately prepared for later combination will be very convenient and useful for determination of various substances or enzyme activities.

Certain specific embodiments of the present invention are illustrated in the following representative examples.

EXAMPLE 1

Determination of Choline Esterase Activity

| Reagent solution | | |
| --- | --- | --- |
| Peroxidase | 1000 | U |
| Butyrylthiocholine | 300 | mg |
| Triton X-100 | 100 | mg |
| Chromogen | | |
| compound No. 41 | 20 | mg (1) |
| compound No. 53 | 20 | mg (2) |
| compound No. 59 | 20 | mg (3) or |
| compound No. 63 | 20 | mg (4) |

These materials are dissolved in 100 ml of 50 mM Tris buffer (pH 7.5).

After the reagent solution is heated at 37° C. for 10 minutes, 10 μl of serum is added thereto, and exactly 2 minutes and 5 minutes thereafter, absorbance of the reaction solution is measured at λmax of the chromogen in contrast with a reagent blank test. A difference between the absorbance 5 minutes thereafter and that 2 minutes thereafter is calculated, and choline esterase activity in serum is calculated by a calibration curve prepared in advance.

Another reagent solution prepared by dissolving peroxidase, butyrylthiocholine and 390 mg of DTNB in said buffer in the same manner as above is also used.

Results are shown in Table 6 in comparison with the measurements according to the system (A) using choline oxidase, peroxidase and o-toluoylcholine as substrate.

TABLE 5

| Serum No. | (ΔpH/hr) | | | | | |
| --- | --- | --- | --- | --- | --- | --- |
| | A | DTNB | (1) | (2) | (3) | (4) |
| 1 | 0.76 | 0.68 | 0.76 | 0.74 | 0.76 | 0.77 |
| 2 | 0.79 | 0.84 | 0.81 | 0.77 | 0.79 | 0.80 |
| 3 | 0.92 | 0.96 | 0.88 | 0.91 | 0.91 | 0.92 |
| 4 | 0.87 | 0.72 | 0.88 | 0.88 | 0.86 | 0.87 |
| 5 | 1.02 | 1.10 | 0.99 | 1.01 | 1.00 | 1.02 |

EXAMPLE 2

Determination of Free Form of Cholesterol

| Reagent solution (A) | |
| --- | --- |
| Peroxidase | 1000 U |
| Triton X-100 | 100 mg |

These materials are dissolved in 100 ml of 50 mM phosphate buffer (pH 6.75) to make reagent solution (A).

| Reagent solution (B) | |
| --- | --- |
| Cholesterol acyltransferase | 1000 U |
| Acyl CoA | 300 mg |
| Triton X-100 | 100 mg |
| Chromogen | |
| compound No. 41 | 20 mg (1) |
| compound No. 53 | 20 mg (2) |
| compound No. 59 | 20 mg (3) |
| compound No. 63 | 20 mg (4) or |
| compound No. 65 | 20 mg (5) |

These materials are dissolved in 100 ml of 50 mM phosphate buffer (pH 6.75) to make reagent solution (B).

Reagent solution (A) and reagent solution (B) are heated at 30° C. for ten minutes. 10 μl of serum sample is added to 1.5 ml of reagent solution (A) and the mixture is incubated at 37° C. for 10 minutes. To the mixture is added 1.5 ml of reagent solution (B). After incubation for 10 minutes, the absorbancy of the reaction solution is measured at λmax of chromogen utilized in comparison with reagent blank as control. The content of free form of cholesterol in serum is determined using a calibration curve prepraed in advance.

The results are shown in Table 6 together with the result obtained according to the method (B) using cholesterol oxidase and peroxidase.

TABLE 6

| Serum No. | B | (1) | (2) | (3) | (4) | (5) |
| --- | --- | --- | --- | --- | --- | --- |
| 1 | 28.7 | 28.5 | 29.0 | 28.7 | 28.7 | 29.1 |
| 2 | 26.3 | 25.9 | 26.1 | 26.1 | 26.4 | 25.8 |
| 3 | 38.2 | 38.0 | 38.1 | 38.3 | 38.3 | 38.0 |
| 4 | 15.4 | 16.1 | 15.5 | 15.5 | 15.2 | 15.2 |
| 5 | 25.9 | 26.3 | 25.9 | 25.8 | 25.8 | 26.1 |

What is claimed is:

1. A method for the determination of a compound having a mercapto group, which comprises reacting said compound with a chromogen represented by formula (I):

wherein Y is hydrogen or hydroxyl; $R_1$, $R_2$ and $R_3$ are independently selected from the group consisting of (II), (III) or (IV):

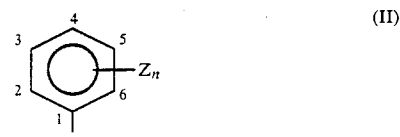

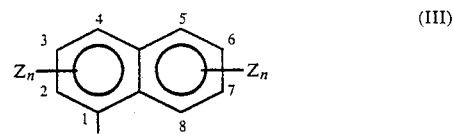

-continued

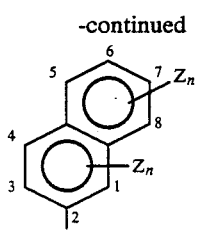
(IV)

wherein Z is independently selected from the group consisting of hydroxyl, optionally substituted amino, optionally substituted $C_{1-5}$ alkyl, $C_{2-5}$ alkenyl, optionally substituted phenyl, optionally substituted naphthyl, $C_{2-5}$ acyl, halogen, nitro, sulfo, carboxyl or $C_{1-4}$ alkoxy; and n is from 0 to 3, provided that at least one Z is hydroxyl or optionally substituted amino, wherein the optional substituents are selected from the group consisting of $C_{1-5}$ alkyl, $C_{2-5}$ alkenyl, phenyl, naphthyl, $C_{1-4}$ alkoxy, hydroxyl, carboxyl, sulfo, sulfonyl, halogen, amino, $C_{1-4}$ alkoxycarbonyl, $C_{1-5}$ aminoalkyl, $C_{2-5}$ acyl and nitro in the presence of peroxidase or thiol oxide reductase and qualitatively or quantitatively determining whether or not pigment is thus formed.

2. A method according to claim 1, wherein $R_1$ and $R_2$ are formula (II).

3. A method according to claim 1, wherein $R_1$ and $R_2$ are formula (II) and $R_3$ is selected from group consisting of (II), (III) and (IV).

4. A method according to claim 1, wherein said mercapto compound is provided by a reaction system which produces a mercapto compound.

5. A method according to claim 4, wherein said reaction system comprises the reaction of acetyl CoA with a second reactant in the presence of an enzyme.

6. A method according to claim 5, wherein said second reactant is a member selected from the group consisting of L-aspartate, chloramphenicol, gentamicin $C_{la}$, gentamicin $C_l$, choline and an amino acid.

7. A method according to claim 1, wherein said determination of pigment is carried out by photometric measurement.

8. A method according to claim 7, wherein said measurement is carried out by measuring the absorption of the reaction solution.

9. A method according to claim 8, wherein said absorption is measured using rays having wavelengths in the visible ray region.

10. A method according to claim 7, wherein said measurement is carried out by measuring the rate of absorption change of the reaction solution.

11. A method according to claim 1, wherein said reaction is carried out in a buffer.

12. A method according to claim 1, using peroxidase and (I).

13. A method according to claim 1, wherein said mercapto compound is a member selected from the group consisting of L-cysteine, glutathione, CoA, methanethiol, dihydrolipoamide and thiocholine.

* * * * *